United States Patent
Sakai et al.

[11] Patent Number: 5,679,817
[45] Date of Patent: Oct. 21, 1997

[54] ALKYLENEDIAMINE-N,N'-DISUCCINIC ACID IRON (III) COMPLEX SALTS AND PROCESS FOR PRODUCTION THEREOF

[75] Inventors: Haruo Sakai; Takashi Sato; Toshitake Yamakawa, all of Otake, Japan

[73] Assignee: Nitto Chemical Industry Co., Ltd., Tokyo, Japan

[21] Appl. No.: 505,461

[22] Filed: Jul. 21, 1995

[30] Foreign Application Priority Data

Jul. 25, 1994 [JP] Japan .................. 6-192248

[51] Int. Cl.⁶ .................. C07F 15/02
[52] U.S. Cl. .................. 556/148
[58] Field of Search .................. 556/148

[56] References Cited

U.S. PATENT DOCUMENTS 5,238,791  8/1993  Tappe .

FOREIGN PATENT DOCUMENTS

| 0532003 | 3/1993 | European Pat. Off. . |
| 0 581 197 | 2/1994 | European Pat. Off. . |
| 27 05 247 | 8/1978 | Germany . |
| 554600 | 3/1993 | Japan . |
| 0574829 | 12/1993 | Japan . |
| 6208213 | 7/1994 | Japan . |
| 7-2745 | 1/1995 | Japan . |
| 1 397 479 | 6/1975 | United Kingdom . |

OTHER PUBLICATIONS

301C Modified Miti Test (1), OECD Chemicals Test Guidelines (1992).
Stereospecific Ligands and Their Complexes, Neal et al, vol. 7, No. 11, Nov. 1968, pp. 2405–2412.
Synthesis and Complex–Forming Properties of Complexons Derived from DiCarboxylic Acids v. Synthesis of Complexons Derived from Succinic Acid, Gorelov et al, Zhurnal Obshchei Kimii 49 (3), pp. 659–663.
European Office Action dated Dec. 5, 1996.
Chemical Abstracts, vol. 101, No. 20, Abstract No. 182607n, p. 735 (1984).

*Primary Examiner*—Porfirio Nazario-Gonzalez
*Attorney, Agent, or Firm*—Cushman Darby & Cushman IP Group of Pillsbury Madison & Sutro LLP

[57] ABSTRACT

(S,S)-ethylenediamine-N,N'-disuccinic acid iron (III) ammonium salt represented by the formula:

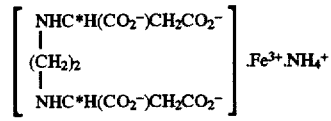

wherein C* is an asymmetric carbon atom. This compound has a very high biodegradability and it is not accumulated in the environment even when used as a photographic processing agent or the like. Therefore, the compound is advantageous for the protection of environment.

8 Claims, 5 Drawing Sheets

ALKYLENEDIAMINE-N,N'-DISUCCINIC ACID IRON (III) COMPLEX SALTS AND PROCESS FOR PRODUCTION THEREOF

BACKGROUND OF THE INVENTION

1. Field of the Invention

The present invention relates to novel alkylenediamine-N,N'-disuccinic acid iron (III) complex salts usable as, for example, a photographic processing agent, and a process for production thereof. In particular, the present invention relates to optically active iron chelate complexes, more specifically, (S,S)-ethylenediamine-N,N'-disuccinic acid iron (III) complex salts, and a process for production thereof.

2. Description of the Related Art

Red prussiate (potassium hexacyanoferrate (III)) was widely used in the past as an oxidizing agent contained in a bleaching solution and a bleaching and fixing solution which were used for printing of color photographs. But owing to the pollution problem, i.e., the presence of cyanogen in a waste solution after development, there are now used iron chelate compounds such as ethylenediaminetetraacetic acid (EDTA) iron (III) complex salts, diethylenetriaminepentaacetic acid (DTPA) iron (III) complex salts, propanediaminetetraacetic acid (PDTA) iron (III) complex salts, etc. However since these iron chelate compounds have a strong chelate bond strength between each acid and iron ions but are poor in biodegradability, they continue to be accumulated in the environment as industrial wastes. Therefore, they have been disadvantageous for use from the viewpoint of the protection of environment.

On the other hand, there have been proposed several chelating agents which are used as a photographic agent and have biodegradability. They include, for example, β-alanine N,N-diacetic acid (EP-A-0574829) and isoserine N,N-diacetic acid (U.S. Pat. No. 5,238,791). These chelating agents, however, have been disadvantageous for use because they have a low iron chelate stability constant of about 10, so that when they are used as a photographic developing agent, iron remains in a film or a print.

SUMMARY OF THE INVENTION

An object of the present invention is to provide a novel iron chelate complex which is rapidly degraded by microorganisms and has a chelate-forming ability similar to that of the conventional chelate compounds (the EDTA iron (III) complex salts, etc.), and a process for producing the same.

The present inventors produced a novel alkylenediamine-N,N'-disuccinic acid iron (III) complex salt. This complex salt is a compound having a chelate-forming ability (iron chelate stability constant: about 20) similar to that of the EDTA iron (III) complex salts, the conventional chelate compounds and a high biodegradability, as compared with β-alanine N,N-diacetic acid and isoserine N,N-diacetic acid.

Aforesaid alkylenediamine-N,N'-disuccinic acid iron (III) complex salt, however, has two asymmetric carbon atoms, so that a conventional process for producing the complex salt via alkylenediamine-N,N'-disuccinic acid produced from an alkylenediamine and maleic acid gives the complex salt as a mixture of racemic modification and mesoisomer in which 3 optical isomers, i.e., (S,S) form, (R,R) form and (S,R) form are present in a ratio of 1:1:2. Of these optical isomers, the (R,R) form requires a conditioning period for biodegradation. Accordingly, the present inventors investigated in further detail the biodegradation of the alkylenediamine-N,N'-disuccinic acid iron (III) complex salt consisting of mesoisomer and racemic modification by microorganisms and consequently found that the alkylenediamine-N,N'-disuccinic acid iron (III) complex salt of (S,S) form, in particular, (S,S)-ethylenediamine-N,N'-disuccinic acid iron (III) ammonium salt is easily biodegradable compound which is much more rapidly degraded by microorganisms than the alkylenediamine-N,N'-disuccinic acid iron (III) complex salt of meso form and that of (R,R) form.

The present invention was made on the basis of this finding.

That is, one aspect of the present invention is directed to an alkylenediamine-N,N'-disuccinic acid iron (III) complex salt represented by the formula (I):

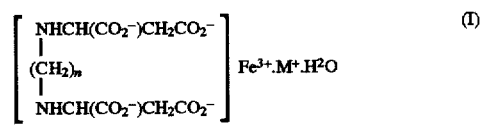

wherein $M^+$ is $K^+$, $Na^+$ or $NH_4^+$, and n is 2 or 3).

Another aspect of the present invention is directed to a process for producing the above-mentioned alkylenediamine-N,N'-disuccinic acid iron (III) complex salt which comprises reacting an ($C_2$–$C_3$)alkylenediamine-N,N'-disuccinic acid with [A] ammonia or an alkali metal hydroxide and [B] metallic iron or an iron compound in an aqueous medium to give a corresponding alkylenediamine-N,N'-disuccinic acid iron (II) ammonium or alkali metal salt, and oxidizing the salt if necessary.

Further another preferable aspect of the present invention is directed to (S,S)-ethylenediamine-N,N'-disuccinic acid iron (III) ammonium salt represented by the formula (II):

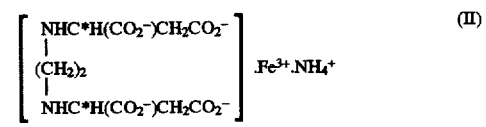

wherein C* is an asymmetric carbon atom.

Still another aspect of the present invention is directed to a process for producing (S,S)-ethylenediamine-N,N'-disuccinic acid iron (III) ammonium salt represented by the above formula (II) which comprises reacting (S,S)-ethylenediamine-N,N'-disuccinic acid with [A] iron or an iron compound and [B] ammonia in an aqueous medium, and oxidizing the reaction product if necessary.

PREFERRED EMBODIMENTS OF THE INVENTION

Figure 1:
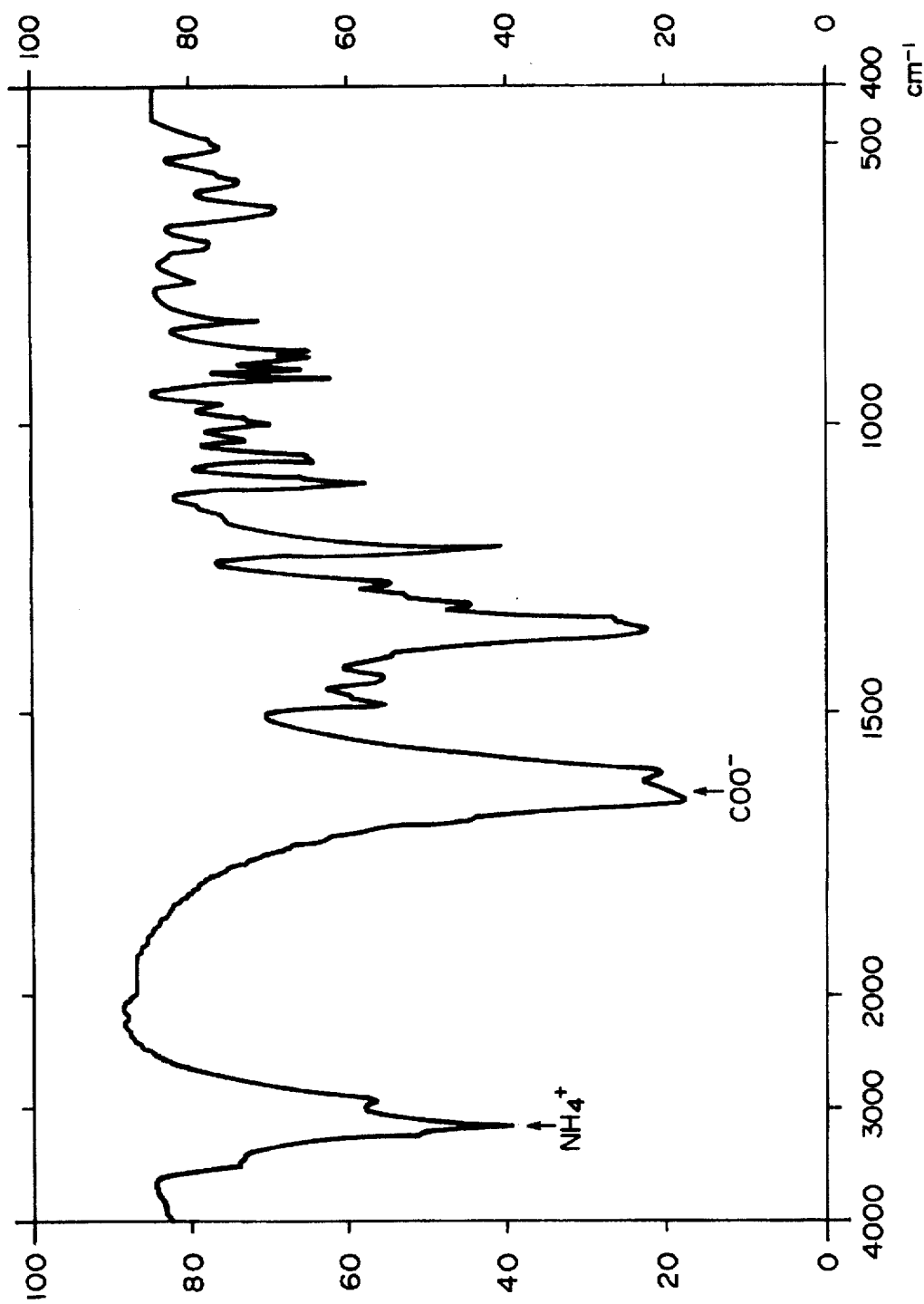
FIG. 1 is an IR spectrum obtained by a KBr tablet method of (S,S)-ethylenediamine-N,N'-disuccinic acid iron (III) ammonium salt synthesized in Example 1.

The present invention is explained below in detail. The alkylenediamine-N,N'-disuccinic acid iron (III) complex salt of the present invention has the structure represented by the formula (I). In the formula (I), M+ denotes an ion of sodium, potassium or ammonium and indicates that a sodium, potassium or ammonium salt is formed. As to the length of the alkyl group connecting the nitrogen atoms, the alkyl group is composed of 2 or 3 methylene groups. Said complex salt has a molecule of water of crystallization.

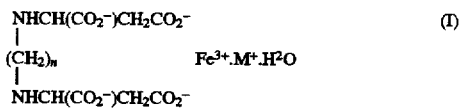

wherein $M^+$ is $K^+$, $Na^+$ or $NH_4^+$, and n is 2 or 3.

The compound of the present invention can be produced as follows. First, an $(C_2-C_3)$alkylenediamine-N,N'-disuccinic acid is reacted with ammonia or an alkali metal hydroxide and an iron (II) salt to give a corresponding alkylenediamine-N,N'-disuccinic acid iron (II) ammonium or alkali metal salt. This reaction is carried out in an aqueous medium at a temperature of 5°–45° C., preferably 25°–35° C. The amount of ammonia or the alkali metal hydroxide used may be properly chosen in a range of 1 to 6 moles, preferably 1.5 to 4.5 moles, per mole of the alkylenediamine-N,N'-disuccinic acid. The amount of the iron (II) salt used may be properly chosen in a range of 0.5 to 1.5 moles, preferably 0.8 to 1 mole, per mole of the alkylenediamine-N,N'-disuccinic acid.

The alkylenediamine-N,N'-disuccinic acid used in the reaction can be synthesized by a conventional method. For example, it can be synthesized by reacting ethylenediamine or propylenediamine with maleic acid or a combination of maleic anhydride and an alkali metal hydroxide with heating (Zhurnal Obshchei Khimii 49 (3) 659–663). As the iron (II) salt, iron (II) sulfate, iron (II) chloride, etc. can be used. Iron (II) sulfate is preferable from the viewpoint of corrosiveness. As the alkali metal hydroxide, hydroxides of sodium, potassium, etc. are preferable.

Then, the alkylenediamine-N,N'-disuccinic acid iron (II) ammonium or alkali metal salt is oxidized into a corresponding iron (III) salt. This oxidation reaction can be carried out by using the aqueous solution of the aforesaid produced iron (II) salt as it is, and reacting therewith an oxidizing agent such as molecular oxygen or a peroxide. The molecular oxygen includes air, oxygen-enriched air, oxygen, etc. Air is usually preferable from an economic viewpoint. A suitable amount of air used is approximately 10–30 times as large as the theoretical equivalent amount with respect to the aforesaid iron (II) salt. As the peroxide, persulfates such as ammonium persulfate, sodium persulfate, potassium persulfate, etc. are preferable. The amount of the peroxide used may be properly chosen in a range of 0.9 to 2.0 equivalents, preferably 1.0 to 1.5 equivalents, per equivalent of the aforesaid iron (II) salt. Although the oxidation reaction can be carried out in an arbitrary pH range of the reaction solution from the acidic range to the alkaline range, it is preferably carried out at pH 5 to 10, more preferably pH 6 to 8. As a pH adjustor, sulfuric acid is preferable. The oxidation reaction temperature is 10°–90° C., preferably 20°–50° C.

The compound of the present invention can be produced also by using metallic powdered iron or a iron (III) salt in place of the iron (II) salt in the above-mentioned reaction. When metallic iron is used, a $(C_2-C_3)$alkylenediamine-N, N'-disuccinic acid is mixed with ammonia or an alkali metal hydroxide in an aqueous medium, followed by adding thereto metallic iron. In this case, the iron component is mainly dispersed in the resulting mixture. Then, an oxidizing agent such as molecular oxygen or a peroxide is reacted with the mixture to oxidize and dissolve the iron component, whereby the alkylenediamine-N,N'-disuccinic acid iron (III) complex salt is produced. When an iron (III) salt is used, the alkylenediamine-N,N'-disuccinic acid iron (III) complex salt is produced by reacting a $(C_2-C_3)$-alkylenediamine-N,N'-disuccinic acid with ammonia or an alkali metal hydroxide and an iron (III) salt. The reaction conditions such as the using amounts of ammonia or the alkali metal hydroxide and metallic iron or the iron (III) salt, the reaction temperature and pH, the oxidation, etc. may be properly chosen in the above-mentioned ranges.

In the present invention, after completion of the reaction, the pH of the reaction solution is adjusted to 4.0 to 6.5, preferably 5.5 to 6.2. This adjustment increases the concentration of by-products produced in the reaction solution and facilitates crystallization of a desired product from the reaction solution. The reaction solution is concentrated until its weight becomes 3 to 5 times the weight of the alkylenediamine-N,N'-disuccinic acid used in the reaction, and the residue is cooled. The thus precipitated crystals of the alkylenediamine-N,N'-disuccinic acid iron (III) complex salt are separated from the mother liquor by means of a centrifuge or the like, washed to be freed of by-products adhering to the crystals, and then dried, whereby the desired product can be obtained. The thus obtained alkylenediamine-N,N'-disuccinic acid iron (III) complex salt has a molecular weight of 380 to 415 and is degradable by microorganisms.

The (S,S)-ethylenediamine-N,N'-disuccinic acid iron (III) ammonium salt of the present invention has a structure represented by the above formula (II) and has such a high biodegradability that it is easily degradable for utilization when tested by the degradability test method, No. 301C Modified MITI Test (1) prescribed in the item of "degradation, concentration" in Chapter 3 of the guidelines for chemicals test of OECD (Organization for Economic Cooperation and Development). Furthermore, this compound has a chelate stability similar to that of ethylenediaminetetraacetic acid iron complexes.

The compound of the present invention can be produced as follows. First, (S,S)-ethylenediamine-N,N'-disuccinic acid is reacted with ammonia or an alkali metal hydroxide and metallic iron or an iron compound to give an (S,S)-ethylenediamine-N,N'-disuccinic acid iron complex salt. This reaction is carried out in an aqueous medium at a temperature of 5°–100° C., preferably 10°–90° C. The amount of ammonia used may be properly chosen in a range of 0.5 to 5 moles, preferably 0.8 to 4.5 moles, per mole of (S,S)-ethylenediamine-N,N'-disuccinic acid. The amount of iron (metallic iron powder) or the iron compound used may be properly chosen in a range of 0.25 to 1.5 moles, preferably 0.3 to 1.2 moles, in terms of iron atoms, per mole of (S,S)-ethylenediamine-N,N'-disuccinic acid.

The (S,S)-ethylenediamine-N,N'-disuccinic acid used in the present invention can be synthesized by a conventional method. For example, it can be synthesized by heating a 1,2-halogenoethane and L-aspartic acid in the presence of an alkali metal hydroxide (Inorganic Chemistry, 7 (11), 2405 (1968)).

The iron source in the present invention is iron powder and iron compounds.

The iron compound includes divalent and trivalent iron compounds, and there can be used iron sulfates; iron halides such as iron chlorides, etc.; iron oxides such as diiron trioxide (i.e. iron (III) oxide) ($Fe_2O_3$), triiron tetraoxide (i.e., black iron oxide) ($Fe_3O_4$), iron (III) hydroxide oxide (FeO(OH)), etc.; and hydrated iron oxides. Of these, triiron tetraoxide is preferable from the viewpoint of reactivity. The above-exemplified iron compounds may be used singly or as a mixture of two or more thereof. The presence of a reducing agent makes it possible to carry out the reaction more rapidly.

Subsequently, when the (S,S)-ethylenediamine-N,N'-disuccinic acid iron complex salt obtained by the reaction contains an iron (II) salt, the iron (II) salt is oxidized into the corresponding ion (III) salt. This oxidation reaction can be carried out by using the aqueous solution of the aforesaid produced iron complex salt as it is, and reacting therewith an oxidizing agent such as molecular oxygen or a peroxide.

The molecular oxygen includes air, oxygen-enriched air, oxygen, etc. Air is usually preferable from an economic viewpoint. The amount of air used is approximately 5–50 times, preferably approximately 10–25 times as large as the theoretical equivalent amount with respect to the aforesaid iron (II) salt.

As the peroxide, persulfates such as ammonium persulfate, sodium persulfate, potassium persulfate, etc. are preferable. The amount of the peroxide used may be properly chosen in a range of 0.9 to 2.0 equivalents, preferably 1.0 to 1.5 equivalents, per equivalent of the aforesaid iron (II) salt.

Although the oxidation reaction can be carried out in an arbitrary pH range of the reaction solution from the acidic range to the alkaline range, it is preferably carried out at pH 4 to 10, more preferably pH 5.0 to 8.0. As a pH adjustor, aqueous ammonia, (S,S)-ethylenediamine-N,N'-disuccinic acid or sulfuric acid is preferably used.

The oxidation reaction temperature is 5°–90° C., preferably approximately 10°–50° C.

After completion of the reaction, the pH of the reaction solution is adjusted to 3.5 to 6.5, preferably 4.5 to 5.5. As the pH adjustor, (S,S)-ethylenediamine-N,N'-disuccinic acid or sulfuric acid is preferably used. This adjustment facilitates crystallization of a desired product from the reaction solution. The reaction solution is concentrated and then cooled to precipitate (S,S)-ethylenediamine-N,N'-disuccinic acid iron (III) ammonium salt as crystals. The reaction solution is preferably concentrated until its weight becomes 1.5 to 5 times, preferably 1.5 to 3.5 times, as large as the weight of the (S,S)-ethylenediamine-N,N'-disuccinic acid used in the reaction. The precipitated crystals are separated from the mother liquor by means of a centrifuge or the like, washed with ice water and then dried, whereby the compound of the above formula, i.e., the desired product can be obtained.

The thus obtained (S,S)-ethylenediamine-N,N'-disuccinic acid iron (III) ammonium salt has a molecular weight of 362 and is very rapidly degradable by microorganisms.

The present invention is explained with reference to the following examples.

EXAMPLE 1

Into a 1-liter cylindrical three-necked flask fitted with a stirrer and a thermometer were charged 146.1 g of (S,S)-ethylenediamine-N,N'-disuccinic acid, 350 g of water and 56.7 g of 15% aqueous ammonia, and stirred at room temperature. Thereto was added 39.1 g of triiron tetraoxide (purity: 98.5%), and the resulting mixture was heated at 85° C. for 30 minutes and then matured as it was for 15 minutes. The reaction mixture was cooled to room temperature and adjusted to pH 7.0 with aqueous ammonia. Air was blown through the reaction mixture at a rate of 7 liters/minute at room temperature for 4 hours to carry out oxidation reaction. Subsequently, the reaction mixture was adjusted to pH 5.0 with (S,S)-ethylenediamine-N,N'-disuccinic acid and then concentrated under reduced pressure until crystals were sufficiently precipitated. The reaction mixture was cooled to 5° C. to precipitate (S,S)-ethylenediamine-N,N'-disuccinic acid iron (III) ammonium salt further. The precipitated crystals were separated with a centrifuge. The wet crystals were washed with a small amount of ice water and then dried at 70° C. for 1 hour and 30 minutes.

The thus obtained (S,S)-ethylenediamine-N,N'-disuccinic acid iron (III) ammonium salt was yellow crystals, and its amount was 126.7 g and its yield 70.0% (based on the amount of triiron tetraoxide).

The results of measurement of the elemental analysis values, ammonia content, chelating agent percentage, and infrared absorption spectrum of the crystals are described below:

1. Elemental analysis values (%)

|  | C | H | N | Fe |
|---|---|---|---|---|
| Found | 33.272 | 4.556 | 11.444 | 15.359 |
| Calculated | 33.171 | 4.447 | 11.606 | 15.426 |

2. Ammonia content
   Found 4.646% (JIS K8960 Kjeldahl distillation method)
   Calculated 4.701%
3. Chelating agent percentage
   Found 79.1% (chelatometoric titration using Zn-XO) Calculated 79.6%
4. Infrared absorption spectrum FIG. 1
   The spectrum in FIG. 1 shows absorptions due to carbonyl and ammonia at 1600–1700 $cm^{-1}$ and near 3200 $cm^{-1}$, respectively.

The above results of measurement of the elemental analysis values, ammonia content, chelating agent percentage and infrared absorption spectrum agree with the theoretical values obtained on the basis of the compositional formula $C_{10}H_{16}N_3O_8Fe$ of (S,S)-ethylenediamine-N,N'-disuccinic acid iron (III) ammonium salt, within the limits of analytical error. Thus, it was confirmed that the compound obtained was that of the present invention. The specific rotation of the compound was $[\alpha]^{20}_D$+30.8 (C=1, 6N•HCl).

EXAMPLE 2

The (S,S)-ethylenediamine-N,N'-disuccinic acid iron (III) ammonium salt (hereinafter referred to as "(S.S)-EDDS iron ammonium salt") obtained in Example 1 was tested for utilization according to Modified MITI Test. The results obtained are shown in Table 1.

COMPARATIVE EXAMPLE 1

Into a 1-liter cylindrical three-necked flask fitted with a stirrer and a thermometer were charged 146.1 g of ethylenediamine-N,N'-disuccinic acid composed of a mixture of mesoisomer and racemic modification, 500.0 g of water, 24 g of 28% aqueous ammonia and 47.5 g of triiron tetraoxide, and heated at 80°–85° C. for 30 minutes, and the resulting mixture was matured as it was for 15 minutes. The reaction mixture was cooled to 60° C. and the remaining iron oxide was filtered off, after which air was blown through the residue at a rate of 7 liters/minute for 3 hours by means of a ball filter to oxidize the remaining divalent iron into trivalent iron. After completion of the reaction, the reaction mixture was adjusted to pH 5.5 with ammonia and then concentrated under reduced pressure until crystals were sufficiently precipitated. The precipitated crystals were filtered and washed with a small volume of water to obtain 80.3 g of primary crystals. The filtrate and the washing were reconcentrated to obtain 83 g of secondary crystals. The primary crystals and the secondary crystals were combined and then dried at 70° C. for 1 hour to obtain 160.0 g of ethylenediamine-N,N'-disuccinic acid iron (III) ammonium salt.

The thus obtained ethylenediamine-N,N'-disuccinic acid iron (III) ammonium salt composed of a mixture of mesoisomer and racemic modification (hereinafter abbreviated as "meso-racemic mixture-EDDS iron ammonium salt") was tested for utilization according to Modified MITI Test. The results obtained are shown in Table 1.

TABLE 1

|  |  | Degree of degradation after 28 days | |
| --- | --- | --- | --- |
|  |  | TOC[1] | BOD[2] |
| Example 2 | (S,S)-EDDS iron ammonium salt | 98% | 71.6% |
| Comparative Example 1 | Meso, racemic mixture-EDDS iron ammonium salt | 24.9% | 16.8% |
| Reference | Aniline | 100% | 73.1% |

[1]total organic carbon
[2]biochemical oxygen demand

EXAMPLE 3

Into a 1-liter cylindrical three-necked flask fitted with a stirrer and a thermometer were charged 146.1 g of (S,S)-ethylenediamine-N,N'-disuccinic acid, 250 g of water and 195 g of 15% aqueous ammonia, and they were stirred at room temperature. Then, 139 g of iron (II) sulfate heptahydrate was dissolved therein with heating, and the resulting solution was cooled to room temperature and adjusted to pH 7.5 with aqueous ammonia. To the reaction solution was added a solution of 57 g of ammonium persulfate in 150 ml of water with stirring at 20°–25° C. over a period of 30 minutes to carry out oxidation reaction. Subsequently, the reaction solution was concentrated under reduced pressure to adjust the ammonium sulfate concentration to about 25 wt %. The concentrate was adjusted to pH 5.0 with sulfuric acid and then cooled to 15° C. to precipitate an iron (III) complex ammonium salt. The precipitated crystals were separated with a centrifuge. The wet crystals were washed with a small amount of ice water and then dried at 70° C. for 1 hour and 30 minutes.

IR spectrum of the obtained crystals agreed with that of the (S,S)-ethylenediamine-N,N'-disuccinic acid iron (III) ammonium salt obtained in Example 1, and its amount was 100.6 g and its yield 55.6% (based on the amount of iron (II) sulfate).

EXAMPLE 4

Into a 1-liter cylindrical three-necked flask fitted with a stirrer and a thermometer were charged 146 g of (S,S)-ethylenediamine-N,N'-disuccinic acid and 250 g of water, and 195 g of 15% aqueous ammonia was added dropwise with stirring to effect dissolution. A solution of 105.5 g of iron (III) chloride tetrahydrate in 200 g of water was added dropwise with stirring and ice-cooling, and the resulting solution was stirred at room temperature for 2 hours to complete the reaction. Then, the reaction solution was adjusted to pH 5.5 with 15% aqueous ammonia and concentrated until its weight became 560 g. The concentrate was cooled to 15° C. and allowed to stand for 24 hours to precipitate crystals. The precipitated crystals were separated with a centrifuge, washed with a small amount of water, and then dried at 40° C. for 3 hours.

IR spectrum of the obtained crystals agreed with that of the (S,S)-ethylenediamine-N,N'-disuccinic acid iron (III) ammonium salt obtained in Example 1, and its amount was 82.9 g and its yield 50.9% (based on the amount of iron (III) sulfate).

EXAMPLE 5

Into a 1-liter cylindrical three-necked flask fitted with a stirrer and a thermometer were charged 153.0 g of 1,3-propanediaminedisuccinic acid (PDDS), 390.0 g of water and 227.1 g of 15% aqueous ammonia, and they were stirred at room temperature to effect dissolution. Then, 132.7 g of iron (II) sulfate heptahydrate (purity: 99.5%) was dissolved therein with heating, and the resulting solution was cooled to ordinary temperature and adjusted to pH 7.0 with aqueous ammonia. To the reaction solution was added 57.05 g (0.25 mol) of ammonium persulfate with stirring at room temperature over a period of about 60 minutes to complete oxidation reaction. The thus obtained reaction solution was adjusted to pH 6.0 with sulfuric acid and concentrated under reduced pressure until its weight became 650 g. The concentrate was cooled to 20° C. to precipitate an iron (III) complex ammonium salt. The precipitated crystals were separated with a centrifuge, washed with a small amount of water, and then dried at 40° C. for 3 hours and 30 minutes. The thus obtained 1,3-propanediaminedisuccinic acid iron (III) complex ammonium salt was yellow crystalline powder, and its amount was 153.5 g and its yield 81.9% (based on the amount of iron (II) sulfate). The results of measurement of the elemental analysis values, infrared absorption spectrum and ammonia content of the crystals are described below:

1. Elemental analysis values (%)

|  | C | N | H | Fe |
| --- | --- | --- | --- | --- |
| Found | 33.007 | 10.700 | 5.095 | 14.10 |
| Calculated | 33.521 | 10.661 | 5.115 | 14.16 |

2. Infrared absorption spectrum (FIG. 2)

Figure 2:
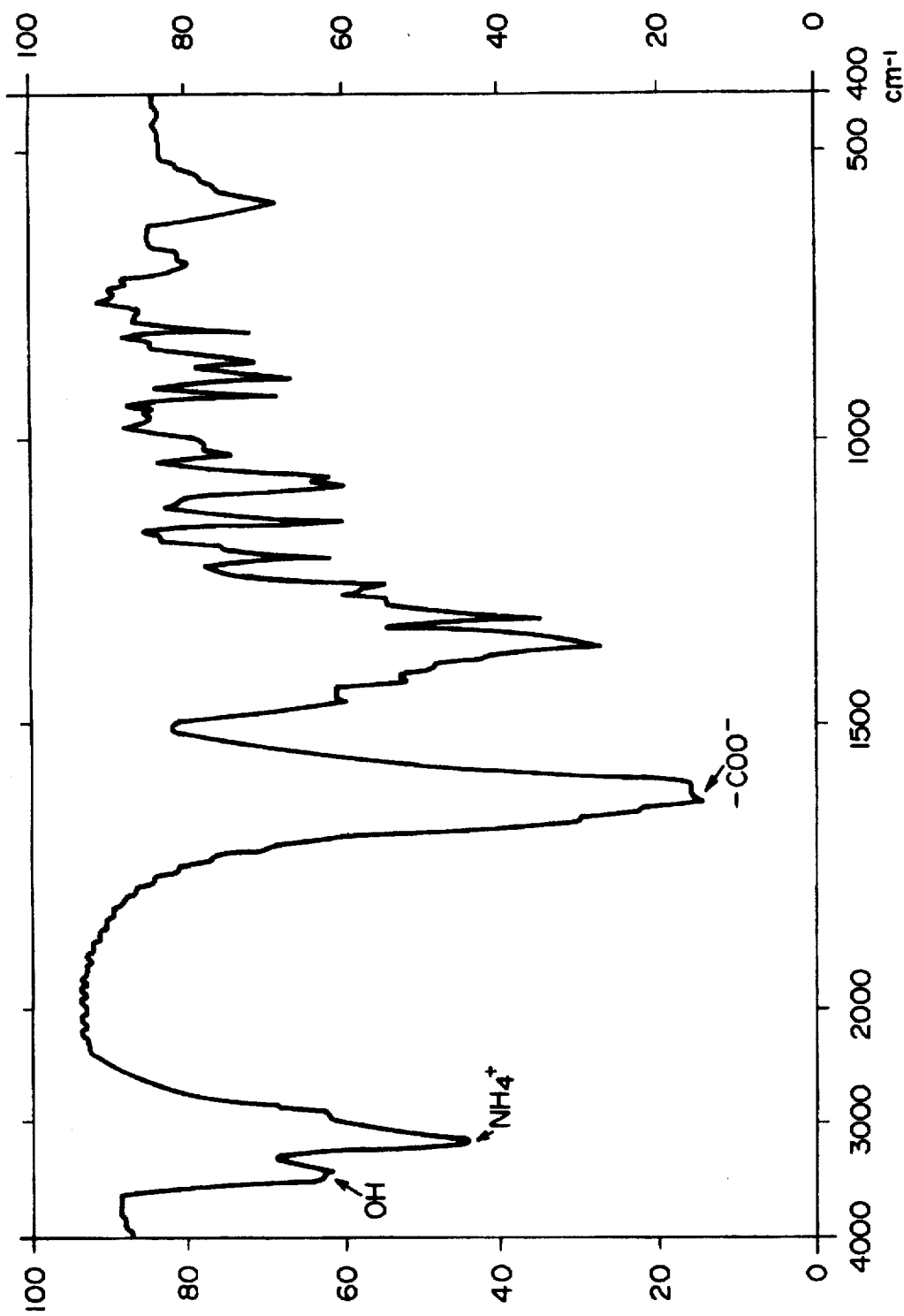
FIG. 2 is an IR spectrum obtained by a KBr tablet method of 1,3-propanediaminedisuccinic acid iron (III) complex ammonium salt synthesized in Example 5.

The spectrum in FIG. 2 shows absorptions due to carbonyl, ammonia and water at 1600–1700 $cm^{-1}$, near 3200 $cm^{-1}$ and near 3500 $cm^{-1}$, respectively.

3. Ammonia content and chelating agent percentage 4.37% (theor. 4.32%) (JIS K8960 Kjeldahl distillation method)

76.0% (theor. 76.6%) (chelatometoric titration using Zn-XO)

The above results of measurement of the elemental analysis values, infrared absorption spectrum and ammonia content agree with the theoretical values obtained on the basis of the compositional formula $C_{11}H_{20}N_3O_9Fe$ of PDDS iron ammonium salt monohydrate, within the limits of analytical error. Thus, it was confirmed that the compound obtained was that of the present invention. A 10% aqueous solution of this compound had a pH of 5.1.

EXAMPLE 6

Into a 1-liter cylindrical flask equipped with a stirrer, air-blowing ball filter, thermometer and material feed opening were charged 153.0 g of 1,3-propanediaminedisuccinic acid, 390.0 g of water and 60.0 g of a 50% aqueous NaOH solution, and they were stirred at room temperature to effect dissolution. Subsequently, 25.8 g of iron powder (purity: 99.5%) was added thereto and then oxidized and solubilized while blowing air through the resulting mixture at room temperature. The unreacted iron powder was filtered off, and the filtrate was adjusted to pH 6.0 and concentrated under reduced pressure until its weight became 750 g. The concentrate was cooled to 20° C. to precipitate an iron (III) complex sodium salt. The precipitated crystals were separated with a centrifuge, washed with a small amount of water, and then dried at 40° C. for 3 hours and 30 minutes. The thus obtained 1,3-propanediaminedisuccinic acid iron (III) complex sodium salt was yellow crystaline powder, and its amount was 130.8 g and its yield 71.2% (based on the amount of the iron powder). The results of measurement of the elemental analysis values, infrared absorption spectrum and sodium content of the crystals are described below:

1. Elemental analysis values (%)

|  | C | N | H | Fe |
|---|---|---|---|---|
| Found | 33.128 | 6.971 | 3.911 | 13.80 |
| Calculated | 33.104 | 7.019 | 4.041 | 13.99 |

2. Infrared absorption spectrum (FIG. 3)

Figure 3:
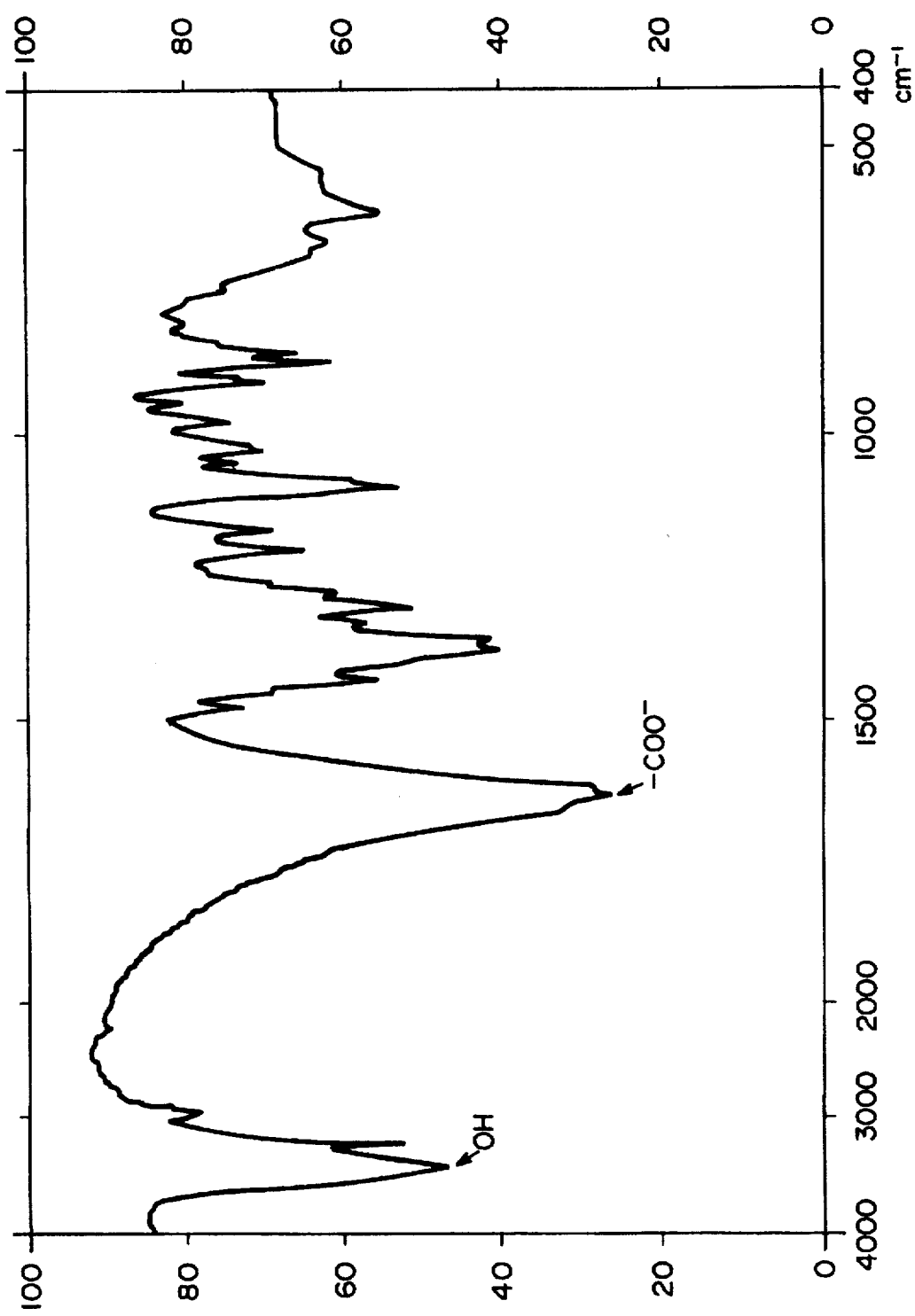
FIG. 3 is an IR spectrum obtained by a KBr tablet method of 1,3-propanediaminedisuccinic acid iron (III) complex sodium salt synthesized in Example 6.

The spectrum in FIG. 3 shows absorptions due to carbonyl and water at 1600–1700 $cm^{-1}$ and near 3500 $cm^{-1}$, respectively.

3. Sodium content and chelating agent percentage 5.8% (theor. 5.76%) (atomic absorption spectrometry)

75.2% (theor. 75.7%) (chelatometoric titration using Zn-XO)

The above results of measurement of the elemental analysis values, infrared absorption spectrum and sodium content agree with the theoretical values obtained on the basis of the compositional formula $C_{11}H_{10}N_2O_9FeNa$ of PDDS iron sodium salt monohydrate, within the limits of analytical error. Thus, it was confirmed that the compound obtained was that of the present invention. A 10% aqueous solution of this compound had a pH of 5.5.

EXAMPLE 7

Into a 1-liter cylindrical flask equipped with a stirrer, thermometer, air-blowing ball filter and material feed opening were charged 146.0 g of ethylenediamine-N,N'-disuccinic acid (EDDS), 370.0 g of water and 227.1 g of 15% aqueous ammonia, and they were stirred at room temperature to effect dissolution. Then, 132.7 g of iron (II) sulfate heptahydrate (purity: 99.5%) was dissolved therein with heating, and the resultig solution was cooled to ordinary temperature and adjusted to pH 7.0 with aqueous ammonia. The solution was subjected to oxidation reaction while blowing air through the reaction solution at room temperature. Thereafter, the reaction solution was adjusted to pH 6.0 with sulfuric acid and concentrated under reduced pressure until its weight became 560 g. Subsequently, this solution was cooled to 20° C. to precipitate an iron (III) complex ammonium salt. The precipitated crystals were separated with a centrifuge, washed with a small amount of water, and then dried at 40° C. for 3 hours and 30 minutes. The thus obtained ethylenediamine-N,N'-disuccinic acid iron (III) complex ammonium salt was yellow crystaline powder, and its amount was 138.4 g and its yield 76.6% (based on the amount of iron (II) sulfate). The results of measurement of the elemental analysis values, infrared absorption spectrum and ammonia content for the crystals are described below:

1. Elemental analysis values (%)

|  | C | N | H | Fe |
|---|---|---|---|---|
| Found | 31.601 | 11.041 | 4.802 | 14.50 |
| Calculated | 31.597 | 11.054 | 4.773 | 14.69 |

2. Infrared absorption spectrum (FIG. 4)

Figure 4:
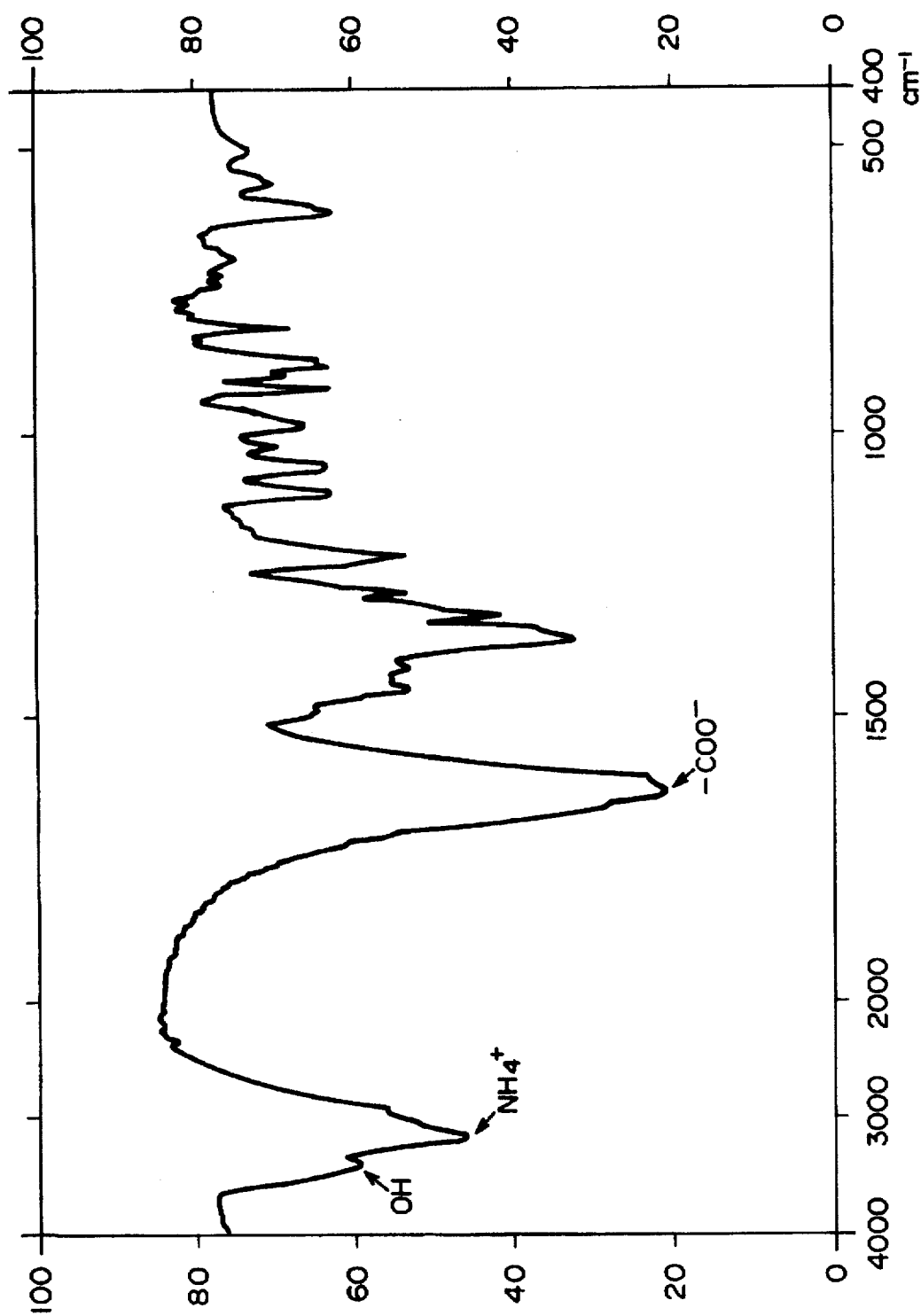
FIG. 4 is an IR spectrum obtained by a KBr tablet method of ethylenediamine-N,N'-disuccinic acid iron (III) complex ammonium salt synthesized in Example 7.

The spectrum in FIG. 4 shows absorptions due to carbonyl and water at 1600–1700 $cm^{-1}$ and near 3500 $cm^{-1}$, respectively.

3. Ammonia content and chelating agent percentage 4.50% (theor. 4.47%) (JIS K8960 Kjeldahl distillation method)

75.6% (theor. 75.83%) (chelatometoric titration using Zn-XO)

The above results of measurement of the elemental analysis values, infrared absorption spectrum and ammonia content agree with the theoretical values obtained on the basis of the compositional formula $C_{10}H_{18}N_3O_9Fe$ of EDDS iron ammonium salt monohydrate, within the limits of analytical error. Thus, it was confirmed that the compound obtained was that of the present invention. The pH value of the 10% solution of this compound was 4.7.

EXAMPLE 8

Into a 1-liter cylindrical three-necked flask fitted with a stirrer and a thermometer were charged 160.6 g of ethylenediamine-N,N'-disuccinic acid and 370.0 g of water, and 176.0 g of an aqueous NaOH solution was added dropwise with stirring and ice-cooling to effect dissolution. A solution of 99.4 g of iron (III) chloride tetrahydrate in 200 g of water was added dropwise with stirring and ice-cooling, and the resulting solution was stirred at room temperature for 2 hours to carry out the reaction. After completion of the reaction, the reaction solution was adjusted to pH 6.0 with 6N hydrochloric acid and concentrated until its weight became 650 g. The concentrate was cooled to 15° C. and allowed to stand for 24 hours to precipitate crystals. The precipitated crystals were separated with a centrifuge, washed with a small amount of water, and then dried at 40° C. for 3 hours and 30 minutes. The thus obtained ethylenediamine-N,N'-disuccinic acid iron (III) complex sodium salt was yellow crystaline powder, and its amount was 78.3 g and its yield 38.4% (based on the amount of iron (III) chloride). The results of measurement of the elemental analysis values, infrared absorption spectrum and sodium content of the crystals are described below:

1. Elemental analysis values (%)

|  | C | N | H | Fe |
|---|---|---|---|---|
| Found | 31.301 | 7.223 | 3.700 | 14.60 |
| Calculated | 31.191 | 7.275 | 3.664 | 14.50 |

2. Infrared absorption spectrum (FIG. 5)

Figure 5:
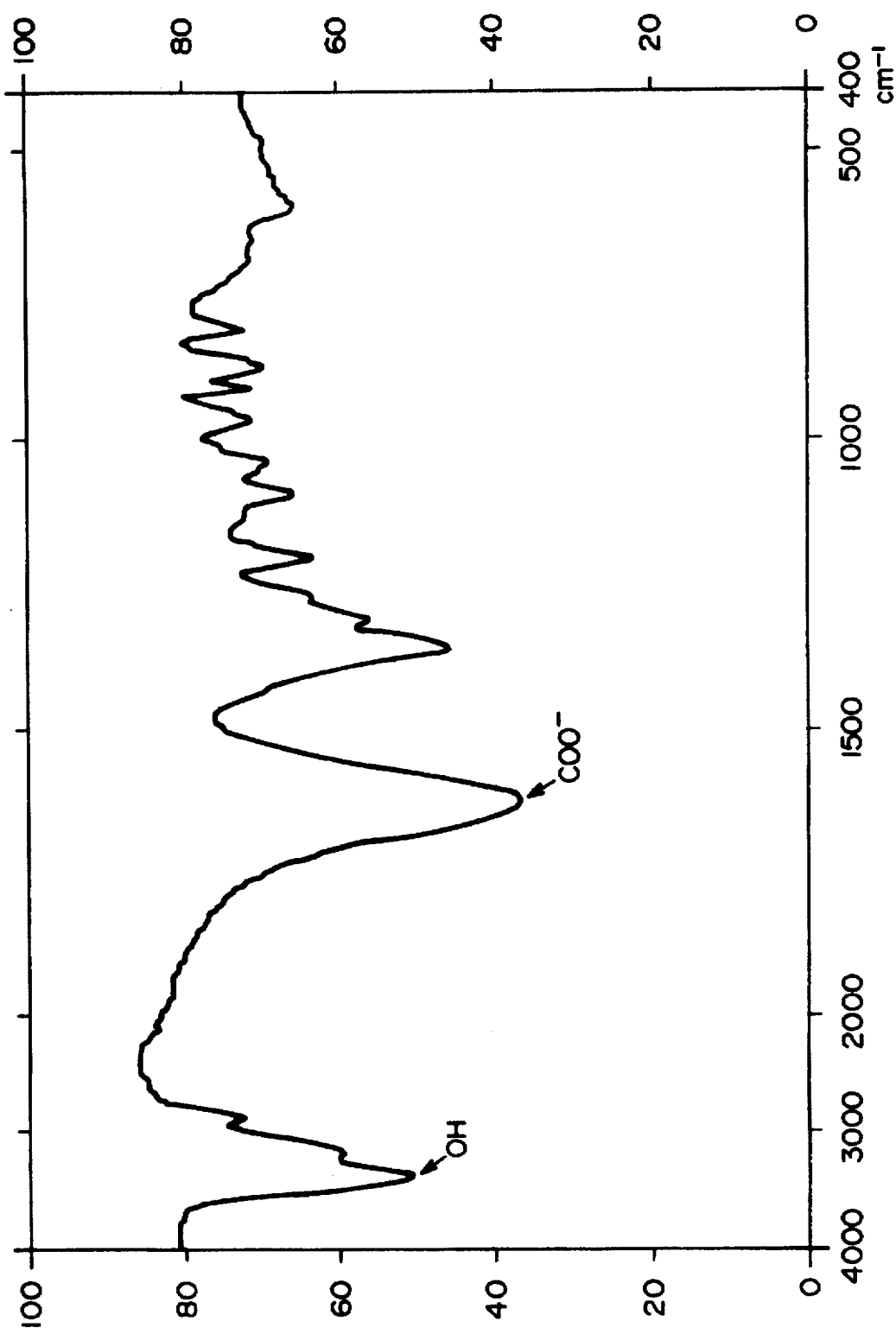
FIG. 5 is an IR spectrum obtained by a KBr tablet method of ethylenediamine-N,N'-disuccinic acid iron (III) complex sodium salt synthesized in Example 8.

The spectrum in FIG. 5 shows absorptions due to carbonyl and water at 1600–1700 $cm^{-1}$ and near 3500 $cm^{-1}$, respectively.

3. Sodium content and chelating agent percentage 6.12% (theor. 5.97%) (atomic absorption spectrometry)

75.2% (theor. 75.7%) (chelatometoric titration using Zn-XO)

The above results of measurement of the elemental analysis values, infrared absorption spectrum and sodium content agree with the theoretical values obtained on the basis of the compositional formula $C_{10}H_{14}N_2O_9FeNa$ of EDDS iron sodium salt monohydrate, within the limits of analytical error. Thus, it was confirmed that the compound obtained was that of the present invention. The pH value of the 10% solution of this compound was 4.9.

EXAMPLE 9

A fluid containing 8 mmols of the 1,3-propanediaminedisuccinic acid iron (III) complex ammonium salt (PDDS•Fe salt) and 8 mmols of $CaCl_2$, 0.25 g of $KH_2PO_4$ and 2.5 g of meat extract as nutrients was dissolved in water and made up to 10 liters. The solution was continuously fed to an activated sludge process equipment (MLSS, 2500–3000 ppm, temperature 20° C.) at a rate of 10 liters/day. As activated sludge, sludge supplied by the sewage treatment plant of Kawasaki city was used. The treated fluid was subjected to liquid chromatography (HPLC) analysis and TOC analysis. Activated sludge treatment was carried out also for the ethylenediamine-N,N'-disuccinic acid iron (III) complex ammonium salt (EDDS•Fe salt) obtained in Example 3, in the same manner as above. The results obtained are shown below. As HPLC value and TOC value, the degradation rate of each substance to be tested and the TOC value of the treated fluid, respectively, are shown. For comparison, there are also shown the results of activated sludge treatment carried out for conventional chelate compounds (EDTA•Fe salt and NTA•Fe salt) according to the method described above. The TOC values of the untreated fluids of each chelate compound were as follows: PDDS•Fe=140 ppm, EDDS•Fe=100 ppm, EDTA•Fe=100 ppm, NTA•Fe=90 ppm.

| Chelate compound (salt) | After 5 days | | After 10 days | | After 20 days | |
|---|---|---|---|---|---|---|
| | HPLC (%) | TOC (ppm) | HPLC (%) | TOC (ppm) | HPLC (%) | TOC (ppm) |
| PDDS.Fe | 25 | 90 | 50 | 80 | 75 | 70 |
| EDDS.Fe | 20 | 95 | 40 | 80 | 70 | 75 |
| EDTA.Fe | 10 | 95 | 10 | 95 | 10 | 95 |
| NTA.Fe | 25 | 70 | 30 | 75 | 50 | 65 |

Japanese Patent Application Nos. 6-192248 and 5-54600 are hereby incorporated in their entirety by reference.

While the foregoing invention has been described in some detail for purposes of clarify and understanding, it will be appreciated by one skilled in the art from a reading of this disclosure that various changes in form and detail can be made without departing from the true scope of the present invention and appended claims.

What is claimed is:

1. A process for producing an alkylenediamine-N,N'-disuccinic acid iron (III) complex salt represented by the formula (I):

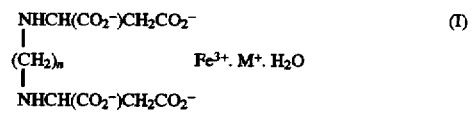

wherein $M^+$ is $K^+$, $Na^+$ or $NH_4^+$, and n is 2 or 3, which comprises reacting an $(C_2$–$C_3)$alkylenediamine-N,N'-disuccinic acid with (A) ammonia or an alkali metal hydroxide and (B) an iron (II) salt in an aqueous medium to give a corresponding alkylenediamine-N,N'-disuccinic acid iron (II) ammonium or alkali metal salt, and oxidizing the salt.

2. A process for producing an alkylenediamine-N,N'-disuccinic acid iron (III) complex salt represented by the formula (I):

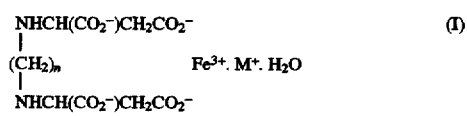

wherein $M^+$ is $K^+$, $Na^+$ or $NH_4^+$ and n is 2 or 3, which comprises reacting an $(C_2$–$C_3)$alkylenediamine-N,N'-disuccinic acid with (A) ammonia or an alkali metal hydroxide and (B) metallic iron in an aqueous medium and subjecting the resulting mixture to oxidation.

3. A process for producing (S,S)-ethylenediamine-N,N'-disuccinic acid iron (III) ammonium salt which comprises reacting (S,S)-ethylenediamine-N,N'-disuccinic acid with iron or an iron compound and ammonia in an aqueous medium.

4. A process according to claim 3, which further comprises oxidizing a reaction product after the reaction in the aqueous medium.

5. A process according to claim 3, wherein the iron compound is selected from the group consisting of iron sulfates, iron chlorides, diiron trioxide, triiron tetraoxide and iron (III) hydroxide oxide.

6. A process according to claim 4, wherein the iron compound is selected from the group consisting of iron sulfates, iron chlorides, diiron trioxide, triiron tetraoxide and iron (III) hydroxide oxide.

7. A process according to claim 3, wherein the iron is used in the form of iron powder.

8. A process according to claim 4, wherein the iron is used in the form of iron powder.

* * * * *